US00PP28838P3

(12) United States Plant Patent
Meinl

(10) Patent No.: US PP28,838 P3
(45) Date of Patent: Jan. 2, 2018

(54) ***HYDRANGEA* PLANT NAMED 'SAXDIFIOROS'**

(50) Latin Name: *Hydrangea macrophylla*
Varietal Denomination: SAXDIFIOROS

(71) Applicant: Kühne Jungpflanzen Claus Kühne, Dresden (DE)

(72) Inventor: Katrin Meinl, Dresden (DE)

(73) Assignee: Kühne Jungpflanzen Claus Kühne, Dresden (DE)

( * ) Notice: Subject to any disclaimer, the term of this patent is extended or adjusted under 35 U.S.C. 154(b) by 13 days.

(21) Appl. No.: 14/999,314

(22) Filed: Apr. 22, 2016

(65) Prior Publication Data

US 2016/0374248 P1 Dec. 22, 2016

Related U.S. Application Data

(60) Provisional application No. 62/230,908, filed on Jun. 18, 2015.

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Keith O Robinson
(74) *Attorney, Agent, or Firm* — Audrey Charles

(57) ABSTRACT

A new and distinct cultivar of *Hydrangea* plant named 'SAXDIFIOROS', characterized by its bright pink-colored inflorescences, dark green-colored foliage, and moderately vigorous, upright growth habit, is disclosed.

1 Drawing Sheet

CROSS-REFERENCE TO RELATED APPLICATIONS

This application claims the benefit of U.S. Provisional Application No. 62/203,908 filed Jun. 18, 2015.

Latin name of genus and species of plant claimed: *Hydrangea macrophylla.*

Variety denomination: 'SAXDIFIOROS'.

BACKGROUND OF THE INVENTION

The present invention relates to a new and distinct cultivar of *Hydrangea* plant botanically known as *Hydrangea macrophylla* and hereinafter referred to by the cultivar name 'SAXDIFIOROS'.

The new cultivar originated in a controlled breeding program in Dresden, Germany during the early summer of 2006. The objective of the breeding program was the development of *Hydrangea* cultivars that have strong stems and long-lasting inflorescences having attractive coloration.

The new *Hydrangea* cultivar is the result of cross-pollination. The female (seed) parent of the new cultivar is a proprietary *Hydrangea macrophylla* breeding selection coded 41-99/1, not patented, characterized by its mophead-type, red-colored inflorescences, medium green-colored foliage, and moderately vigorous, upright growth habit. The male (pollen) parent of the new cultivar is *Hydrangea macrophylla* 'Semperflorens', not patented, characterized by its mophead-type, soft-pink colored inflorescences, light-green colored foliage, and moderately vigorous, upright growth habit. The new cultivar was discovered and selected as a single flowering plant within the progeny of the above stated cross-pollination during April 2008 in a controlled environment in in Dresden, Germany.

Asexual reproduction of the new cultivar by softwood cuttings since June 2008 in Dresden, Germany has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'SAXDIFIOROS' as a new and distinct cultivar of *Hydrangea* plant:

1. Bright pink-colored inflorescences;
2. Dark green-colored foliage; and
3. Moderately vigorous, upright growth habit.

Plants of the new cultivar differ from plants of the female parent primarily in inflorescence color and shade of foliage color. Plants of the new cultivar differ from plants of the male parent primarily in shade of inflorescence color, shade of foliage color and stem strength. Plants of the new cultivar have stronger stems than the male parent.

Of the many commercially available *Hydrangea* cultivars, the most similar in comparison to the new cultivar is ENDLESS SUMMER 'Bailmer', U.S. Plant Pat. No. 15,298. However, in side-by-side comparison, plants of the new cultivar differ from plants of 'Bailmer' in at least the following characteristics:

1. Plants of the new cultivar have an inflorescence color that is a different shade of pink from plants of 'Bailmer';
2. Plants of the new cultivar have sterile floret sepals that are larger than plants of 'Bailmer'; and
3. Plants of the new cultivar have stronger stems than plants of 'Bailmer'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'SAXDIFIOROS'. The plants were grown in 13.0 cm containers for approximately ten months in Dresden, Germany. Detailed growing conditions are described in the following section.

DETAILED BOTANICAL DESCRIPTION

Figure 1:
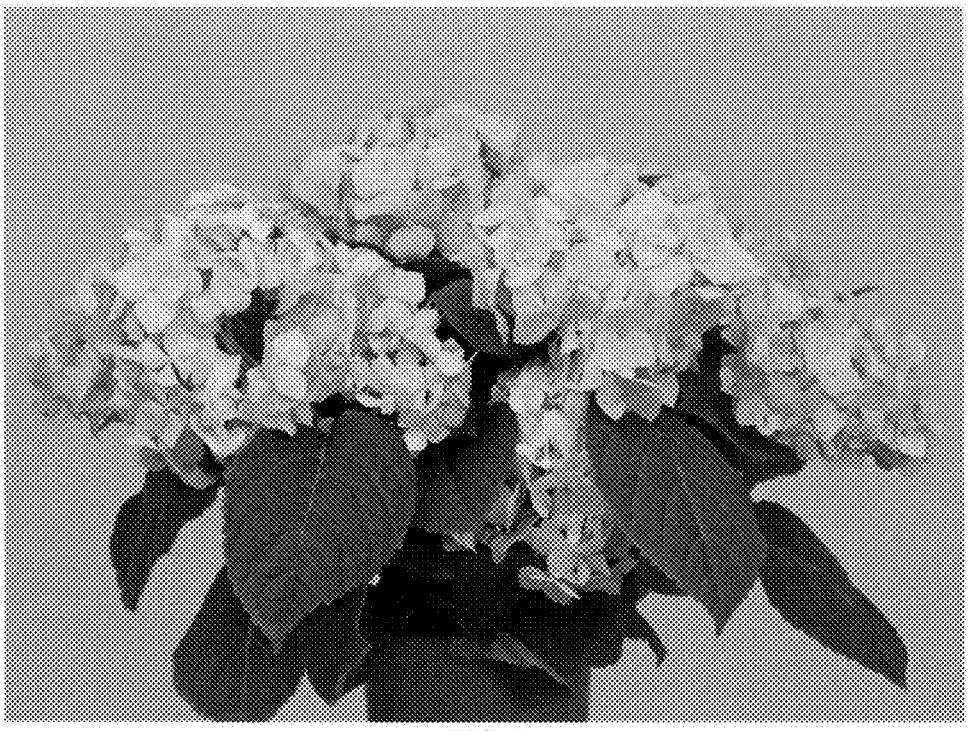
FIG. 1 illustrates a side view of the overall growth and flowering habit of 'SAXDIFIOROS'.
Figure 2:
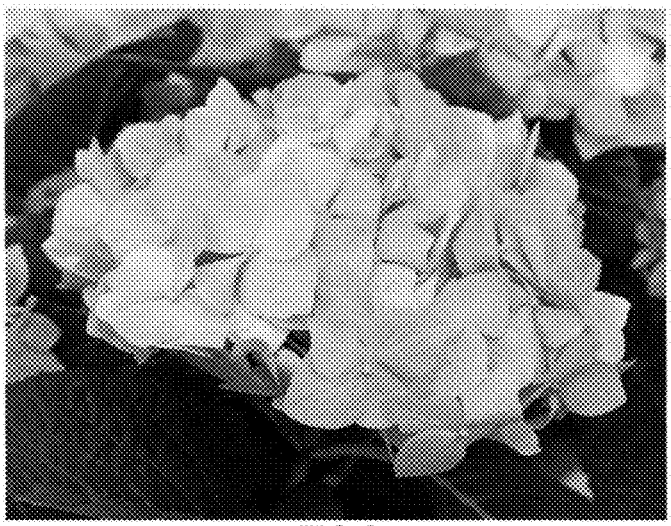
FIG. 2 illustrates a close-up view of an inflorescence of 'SAXDIFIOROS'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The plant history was taken in February 2016 on plants grown in 13.0 cm containers for approximately ten months in Dresden, Germany. Plants were grown outside and then forced to flowering in a greenhouse for an 11 week period. During the forcing period greenhouse temperatures ranged from 64° F. to 75° F. (18° C. to 24° C.) with 3,500 klx/qm supplemental lighting. Plants were treated five times with 0.3% of the growth regulator Dazide, two times during outside cultivation and three times during the forcing period. Plants were pinched twice, five weeks after sticking the unrooted cutting, and then six weeks after transplant to the 13 cm pot. Observations were made when the plants were in natural daylight conditions in Boskoop, The Netherlands. Measurements and numerical values represent averages of typical plants.

Botanical classification: *Hydrangea macrophylla* 'SAXDIFIOROS'.

Parentage:

*Female parent.*—Proprietary *Hydrangea macrophylla* breeding selection coded 41-99/1, not patented.

*Male parent.*—*Hydrangea macrophylla* 'Semperflorens', not patented.

Propagation:

*Type cutting.*—Terminal stem cuttings.

*Time to initiate roots during the summer.*—Approximately 16 days.

*Time to produce a rooted cutting during the summer.*—Approximately 28 days.

*Time to initiate roots during the winter.*—Approximately 18 days.

*Time to produce a rooted cutting during the winter.*—Approximately 31 days.

*Root description.*—Medium thickness, fibrous.

*Rooting habit.*—Moderate branching and density.

Plant description:

*Commercial crop time.*—Approximately 30 to 34 weeks of cultivation from a rooted cutting followed by 9 to 11 weeks of forcing to finish in a 13.0 cm pot.

*Growth habit and general appearance.*—Deciduous shrub, mophead type *Hydrangea.* Moderately vigorous, upright.

*Hardiness.*—USDA Zone 5a (−20° F. to −15° F.).

*Heat tolerance.*—Regularly tolerates temperatures as high as 38° C. in the summer.

*Size.*—Height from soil level to top of plant plane: Approximately 24.0 cm. Width: Approximately 40.0 cm.

*Branching habit.*—Moderately freely branching. Pinching enhances branching. Quantity of lateral branches per plant: Approximately 10.

*Branch.*—Shape: Rounded. Strength: Strong. Fasciation: Absent. Length to base of inflorescence: Approximately 10.0 cm. Diameter: Approximately 5.0 mm. Length of central internode: Approximately 3.3 cm. Texture of young stem: Glabrous. Texture of mature stem: Woody. Color of young stem: 143C, strongly tinged with N186C at the nodes. Color of mature stem: 199A to 199B.

*Lenticels.*—Quantity per internode: Approximately 15. Shape: Round to elliptic, positioned vertically. Size: Approximately 0.5 mm to 1.5 mm. Color: N186C.

Foliage description:

*General description.*—Quantity of leaves per lateral branch: Approximately 8. Fragrance: None detected. Form: Simple. Arrangement: Opposite.

*Leaves.*—Aspect: Flat. Shape: Ovate to elliptic. Margin: Serrated. Apex: Apiculate. Base: Attenuate. Venation pattern: Pinnate. Length of mature leaf: Approximately 12.7 cm. Width of mature leaf: Approximately 8.7 cm. Texture of upper and lower surfaces: Moderately rugose, glabrous. Variegation: Absent. Color of upper surface of young foliage: 143A with venation of 144A to 144B. Color of lower surface of young foliage: Closest to but more yellow than 143A with venation of 144A to 144B. Color of upper surface of mature foliage: Closest to but darker than NN137A with venation of 144A to 144B. Color of lower surface of mature foliage: NN137C to NN137D with venation of 144A to 144B.

*Petiole.*—Length: Approximately 2.2 cm. Diameter: Approximately 3.5 mm. Texture: Glabrous. Color: 144A to 144B.

Flowering description:

*Flowering habit.*—Seasonal, May through August.

*Lastingness of individual inflorescence on the plant.*—Approximately 1.5 months.

Inflorescence description:

*General description.*—Type: Terminal globular, single-type, mophead, compound corymb of fertile florets and rotate-shaped, sterile, sepalous florets borne on the same corymb, persistent. Sterile florets occasionally have visible reproductive parts, but lack an ovary. Quantity per plant: Approximately 5. Fragrance: None detected. Aspect: Facing upward and outward. Height: Approximately 8.2 cm. Width: Approximately 14.9 cm. Quantity of fertile florets per inflorescence: Approximately 20. Quantity of sterile florets per inflorescence: Approximately 85.

*Peduncle.*—Strength: Strong. Shape: Rounded. Length: Approximately 3.6 cm. Diameter: Approximately 3.0 mm. Texture: Matte, densely covered with thin pubescence having an average length 0.5 mm, white in color. Color: 182B.

Floret description:

*General description.*—Type: Single, sterile and fertile.

*Sterile florets, bud just before opening.*—Shape: Ovate. Length: Approximately 9.0 mm. Diameter: Approximately 5.0 mm. Color: 62C.

*Sterile florets.*—Depth: Approximately 8.0 mm. Diameter: Approximately 3.6 cm. Corolla: 4 petals, often closed forming a central eye. Shape: Rotate, cruciform. Diameter: Approximately 2.0 mm. Calyx: 4 sepals, occasionally 3 or 5. Shape: Rotate, cruciform. Diameter: Approximately 3.6 cm.

*Petals, sterile florets.*—Shape: Ovate when open, otherwise petals form a center eye of up to 2.0 mm in diameter and 73B in color. Margin: Entire. Apex: Acute. Base: Cuneate. Length: Approximately 1.8 mm. Width: Approximately 0.8 mm. Texture of upper and lower surfaces: Glabrous, matte. Color of upper surface: 63B. Color of lower surface: 64C.

*Sepals, sterile florets.*—Shape: Broadly ovate to deltoid. Margin: Entire. Apex: Broadly acute. Base: Broadly attenuate. Length: Approximately 2.0 cm. Width: Approximately 2.1 cm. Texture of upper and lower surfaces: Glabrous, matte. Color of upper surface when first open: 64D. Color of lower surface when first open: 63C. Color of upper surface when fully open: Closest to but lighter than 63B. Color of lower surface when fully open: 63C.

*Pedicel, sterile florets.*—Strength: Moderately strong. Aspect: Approximately 40° from peduncle axis. Length: Approximately 1.9 cm. Diameter: Approximately 1.0 mm. Texture: Densely pubescent with appressed hairs having an average length of 0.5 mm, white in color. Color: 63A to 63B.

*Fertile florets, bud just before opening.*—Shape: Broadly obovate. Length: Approximately 4.0 mm. Diameter: Approximately 3.0 mm. Color: 62B, base of 145D.

*Fertile florets.*—Conspicuousness: Inconspicuous. Depth: Approximately 5.0 mm. Diameter: Approximately 7.0 mm. Corolla: 4 to 5 petals, often vestigial. Shape: Rotate, concave. Diameter: Approximately 6.0 mm. Calyx: Approximately 5 sepals. Shape: Rotate. Diameter: Approximately 4.0 mm.

*Petals, fertile florets.*—Shape: Ovate. Margin: Entire. Apex: Acute. Base: Truncate. Length: Approximately 2.0 mm. Width: Approximately 1.5 mm. Texture of upper and lower surfaces: Glabrous, matte. Color of upper surface: 63C. Color of lower surface: 63D.

*Sepals, fertile florets.*—Shape: Ovate to deltoid. Margin: Entire. Apex: Acute. Base: Broadly cuneate. Length: Approximately 1.0 mm. Width: Approximately 1.0 mm. Texture of upper surface: Glabrous, matte. Texture of lower surface: Sparsely pubescent. Color of upper and lower surfaces: 158D tinged with 145D.

*Pedicel, fertile florets.*—Strength: Strong. Aspect: Erect. Length: Approximately 4.0 mm. Diameter: Approximately 1.0 mm. Texture: Sparsely pubescent with appressed hairs, white in color. Color: 150D tinged with 62C to 62D.

*Reproductive organs.*—Observed in fertile florets and occasionally in the center of sterile florets, sterile florets lack an ovary. Androecium: Stamen quantity: 8 to 10 per floret. Stamen length: Approximately 2.5 mm to 3.0 mm. Filament color: 85B. Anther shape: Kidney-shaped, basally attached. Anther length: Approximately 1.0 mm. Anther color: 85D. Pollen amount: Moderately abundant. Pollen color: 159D. Gynoecium: Pistil quantity: 1 per floret. Pistil length: Approximately 1.8 mm. Stigma shape: Club-shaped. Stigma color: 77B. Style length: Approximately 1.25 mm, two or three-lobed. Style color: 85D. Ovary length: Approximately 1.5 mm. Ovary texture: Sparsely pubescent with appressed hairs, white in color. Ovary color: 150D tinged with 62D.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'SAXDIFIOROS', substantially as herein illustrated and described.

* * * * *